United States Patent [19]
Dean

[11] Patent Number: 5,783,170
[45] Date of Patent: Jul. 21, 1998

[54] PEPTIDE-METAL CHELATE CONJUGATES

[75] Inventor: Richard T. Dean, Bedford, N.H.

[73] Assignee: Diatide, Inc., Londonderry, N.H.

[21] Appl. No.: 241,625

[22] Filed: May 12, 1994

Related U.S. Application Data

[63] Continuation-in-part of Ser. No. 807,062, Nov. 27, 1991, Pat. No. 5,443,815.

[51] Int. Cl.$^6$ .................. A61K 51/00; A61M 36/14
[52] U.S. Cl. .................. 424/1.69; 530/300; 530/311; 424/1.65; 534/10; 534/14
[58] Field of Search ............... 424/1.11, 1.69, 424/9.1, 9.3, 9.323, 9.4, 1.65; 206/569, 223, 570; 534/10, 14, 15, 16; 530/300, 324, 325, 326, 327, 328, 329, 330, 333, 334, 338

[56] References Cited

U.S. PATENT DOCUMENTS

| | | | |
|---|---|---|---|
| 4,235,886 | 11/1980 | Friedinger . | |
| 4,434,151 | 2/1984 | Byrne et al. . | |
| 4,444,690 | 4/1984 | Fritzberg . | |
| 4,472,509 | 9/1984 | Gansow et al. . | |
| 4,485,101 | 11/1984 | Coy et al. . | |
| 4,571,430 | 2/1986 | Byrne et al. | 424/1.11 |
| 4,575,556 | 3/1986 | Byrne et al. . | |
| 4,611,054 | 9/1986 | Friedinger . | |
| 4,612,366 | 9/1986 | Nutt . | |
| 4,668,503 | 5/1987 | Hnatowich . | |
| 4,732,684 | 3/1988 | Tolman . | |
| 4,832,940 | 5/1989 | Eng et al. . | |
| 4,853,371 | 8/1989 | Coy et al. . | |
| 4,861,869 | 8/1989 | Nicolotti et al. . | |
| 4,871,717 | 10/1989 | Coy et al. . | |
| 4,904,642 | 2/1990 | Coy et al. . | |
| 4,925,650 | 5/1990 | Nosco et al. . | |
| 4,943,523 | 7/1990 | Stavrianopoulos . | |
| 4,965,392 | 10/1990 | Fritzberg et al. . | |
| 4,986,979 | 1/1991 | Morgan et al. . | |
| 5,061,641 | 10/1991 | Shochat et al. . | |
| 5,091,514 | 2/1992 | Fritzberg et al. . | |
| 5,095,111 | 3/1992 | Lever et al. . | |
| 5,112,953 | 5/1992 | Gustavson et al. . | |
| 5,175,257 | 12/1992 | Kasina et al. . | |
| 5,180,816 | 1/1993 | Dean et al. . | |
| 5,196,515 | 3/1993 | Lever et al. . | |
| 5,225,180 | 7/1993 | Dean et al. | 424/1.69 |
| 5,248,764 | 9/1993 | Flanagan et al. . | |
| 5,382,654 | 1/1995 | Lyle et al. | 534/10 |
| 5,405,597 | 4/1995 | Dean et al. | 424/1.69 |
| 5,443,815 | 8/1995 | Dean et al. | 424/1.69 |
| 5,508,020 | 4/1996 | Dean et al. | 424/1.69 |
| 5,620,675 | 4/1997 | McBride et al. | 424/1.69 |
| 5,632,969 | 5/1997 | Flanagan et al. | 424/1.69 |

FOREIGN PATENT DOCUMENTS

| | | |
|---|---|---|
| 84109831.2 | 3/1985 | European Pat. Off. . |
| 86100360.6 | 7/1986 | European Pat. Off. . |
| 87300426.1 | 9/1987 | European Pat. Off. . |
| 87118142.6 | 6/1988 | European Pat. Off. . |
| 88104755.9 | 9/1988 | European Pat. Off. . |
| 90302760.5 | 9/1990 | European Pat. Off. . |
| 90304551.6 | 10/1990 | European Pat. Off. . |
| 90306428.5 | 12/1990 | European Pat. Off. . |
| 90402206.8 | 2/1991 | European Pat. Off. . |
| WO9101144 | 2/1991 | European Pat. Off. . |
| 91104845.2 | 10/1991 | European Pat. Off. . |
| 483704A1 | 5/1992 | European Pat. Off. . |
| 92810381.1 | 11/1992 | European Pat. Off. . |
| 8927255.3 | 6/1990 | United Kingdom . |
| WO8503231 | 8/1985 | WIPO . |
| 8802276 | 1/1989 | WIPO . |
| WO8907456 | 8/1989 | WIPO . |
| WO8909405 | 10/1989 | WIPO . |
| 8901854 | 11/1989 | WIPO . |
| WO8901854 | 12/1989 | WIPO . |
| WO9006323 | 6/1990 | WIPO . |
| WO9010463 | 9/1990 | WIPO . |
| WO9015818 | 12/1990 | WIPO . |
| WO9109876 | 7/1991 | WIPO . |
| 9103116 | 11/1991 | WIPO . |
| 9201027 | 8/1992 | WIPO . |
| 9204559 | 12/1992 | WIPO . |
| WO9212819 | 7/1993 | WIPO . |
| WO9315770 | 8/1993 | WIPO . |
| WO9321151 | 10/1993 | WIPO . |
| 9500553 | 1/1995 | WIPO . |
| 9529708 | 11/1995 | WIPO . |
| 9531221 | 11/1995 | WIPO . |
| 9533497 | 12/1995 | WIPO . |
| 9533498 | 12/1995 | WIPO . |

OTHER PUBLICATIONS

Pearson et al (1996). J. Med Chem., vol. 39, No. 7, pp. 1361–1371 "Somatostatin Receptor-Binding Peptides Labeled with Technetium-99m: Chemistry and Initial Biological Studies".

Rhodes, 1974, "Considerations in the Radiolabeling of Albumin", Sem. Nucl. Med. 4: 281–293.

(List continued on next page.)

*Primary Examiner*—John Kight
*Assistant Examiner*—Dameron Jones
*Attorney, Agent, or Firm*—McDonnell Boehnen Hulbert & Berghoff

[57] ABSTRACT

This invention relates to diagnostic and radiodiagnostic agents, including radiolabeled scintigraphic imaging agents, and therapeutic and radiotherapeutic agents. The invention provides such agents and reagents for preparing such agents, and methods for producing and using such reagents. Specifically, the invention provides radiolabeled imaging agents and non-radioactively labeled imaging agents for imaging sites in a mammalian body and reagents for preparing these imaging agents. The invention also provides radiolabeled therapeutic agents, as well as non-radioactively labeled therapeutic agents, and reagents and methods for preparing these agents. The agents and reagents provided comprise a specific binding peptide, covalently linked to a metal ion-complexing moiety. Reagents, methods and kits for making such reagents, methods for labeling such reagents, and methods for using such labeled reagents are provided.

23 Claims, 1 Drawing Sheet

OTHER PUBLICATIONS

Davidson et al., 1981, "A New Class of Oxotechnetium(5+) Chelate Complexes containing a TcON$_2$S$_2$ Core", *Inorg. Chem. 20:* 1629–1632.

Fritzberg et al., 1982, "Synthesis anbd Biological Evaluation of Tc–99m N,N'–Bis(mercaptoacetyl)–2,3–diaminopropanoate: A Potential Replacement for [$^{131}$I]o–iodohippurate", *J. Nucl. Med. 23:* 592–598.

Byrne and Tolman, 1983, "Technetium–99m Bifunctional Chelating Agent—Thiolactone for Coupling to Biomolecules, N$_2$S$_2$ Ligand for Chelation to Technetium", *J. Nucl. Med. 24:* P126.

Bryson et al., 1988, "Neutral Technetium(V) Complexes with Amide–Thiol–Thioether Chelating Ligands", *Inorg. Chem. 27:* 2154–2161.

Misra et al., 1989, "Synthesis of a Novel Diaminodithiol Ligand for Labeling Proteins and Small Molecules with Technetium–99m", *Tet. Lett. 30:* 1885–1888.

Bryson et al., 1990, "Protecting Groups inb the Preparation of Thiolate Complexes of Technetium", *Inorg. Chem. 29:* 2948–2951.

Knight et al., 1990, "Thrombus Imaging with Tc–99m Synthetic peptides Reactive with Activated Platelets", *J. Nucl. Med. 31:* 757 #209.

Bakker et al., 1990, "Receptor Scintigraphy with a Radioiodinated Somatostatin Analogue: Radiolabeling, Purification, Biologic Activity, and In Vivo Application in Animals", *J. Nucl. Med. 31:* 1501–1509.

Bakker et al., 1991, "In Vivo Use of a Radioiodinated Somatostatin Analogue: Dynamics, Metabolism, and Binding to Somatostatin Receptor–Positive Tumors in Man", *J. Nucl. Med. 32:* 1184–1189.

Kwekkeboom et al., 1991, "[In–111–DTPA–D–Phe]$^1$–Octreotide Scintigraphy in Neuro–endocrine Tumors", *J. Nucl. Med. 32:* 981, Abstract #305.

Faglia et al., 1991, "In Vivo Detection of Somatostatin Receptors in Patients with Functionless Pituitary Adenomas by Means of a Radioiodinated Analog of Somatostatin ([$^{123}$I]–SDZ 204–090)", *J. Clin. Endocrinol. Metab. 73:* 850–856.

Albert et al., 1991, "A Somatostatin Ananlogue to Image SS–Receptor–Positive Tumors: [$^{111}$In–DTPA–DPhe]$^1$–Octreotide (SDZ 215–811)", Abstract LM10, 12th American Peptide Symposium.

Cox et al., 1991, "Technetium Labeled Somatostatin: A Potential Agent for In Vivo Tumor Localization", Abstract, 7th International Symposium on Radiopharmacology, p. 16.

Schwartz et al., 1991, "Preparation of Hydrazino–Modified Proteins and Their Use for the Synthesis of $^{99m}$Tc–Protein Conjugates", *Bioconjugate Chem. 2:* 333.

Krenning et al., 1992, "Somatostatin Receptor Scintigraphy with Indium–111–DTPA–D–Phe–1–Octreotide in Man: Metabolism, Dositometry and Comparison with Iodine–123–Tyr–3–Octreotide", *J. Nucl. Med. 33:* 652–658.

Bomanji et al., 1992, "A Scintigraphic Comparison of Iodine–123–Metaiodobenzylguanidine and an Iodine–Labeled Somatostatin Analog (Tyr–3–Octreotide) in Metastatic Carcinoid Tumors", *J. Nucl. Med. 33:* 1121–1124.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: Disulfide-bond
        ( B ) LOCATION: 3...14
        ( D ) OTHER INFORMATION: /label=disulfide
          / note="The sidechain sulfur atoms of the cysteine residues are linked by a disulfide bond."

( x i ) SEQUENCE DESCRIPTION: SEQ ID NO:1:

```
Ala  Gly  Cys  Lys  Asn  Phe  Phe  Trp  Lys  Thr  Phe  Thr  Ser  Cys
 1             5                            10
```

PEPTIDE-METAL CHELATE CONJUGATES

This application is a continuation-in-part of U.S. patent application Ser. No. 07/807,062, filed Nov. 27, 1991, now U.S. Pat. No. 5,443,815.

BACKGROUND OF THE INVENTION

1. Field of the Invention

This invention relates to therapeutic agents, radiotherapeutic agents, radiodiagnostic agents, and non-radioactive diagnostic agents, and methods for producing such diagnostic and therapeutic agents. The invention also relates to cyclic peptides which specifically bind to somatostatin receptors expressed at the surface of mammalian cells, particularly neoplastic or metastatic mammalian cells. The invention in one aspect relates to scintigraphic imaging agents for imaging sites in a mammalian body. In this aspect, the imaging agents comprise a specific-binding peptide that specifically binds to somatostatin receptor-expressing cells in vivo, labeled with technetium-99m (Tc-99m) via a radiolabel-binding moiety which forms a complex with Tc-99m. In another aspect, the invention provides radioiodinated imaging agents. The invention also provides therapeutic agents, including radioiodinated agents, radioactive metal-reagent complexes and nonradioactive metal-reagent complexes, all of which have therapeutic utility. The invention provides reagents for preparing each of the diagnostic and therapeutic embodiments of the diagnostic and therapeutic agents of the invention, the radiolabeled embodiments and non-radioactive metal complexes thereof, methods for labeling said reagents and kits comprising non-radioactive embodiments of the reagents of the invention and other components for the convenient preparation of the radiolabeled diagnostic and therapeutic agents of the invention.

2. Description of the Prior Art

Somatostatin is a tetradecapeptide that is endogenously produced by the hypothalamus and pancreas in humans and other mammals. The peptide has the formula:

Freidinger, U.S. Pat. No. 4,611,054 disclose cyclic hexapeptide somatostatin analogues useful in the treatment of a number of diseases in humans.

Nutt, U.S. Pat. No. 4,612,366 disclose cyclic hexapeptide somatostatin analogues useful in the treatment of a number of diseases in humans.

Coy et al., U.S. Pat. No. 4,853,371 disclose synthetic octapeptide somatostatin analogues.

Coy and Murphy, U.S. Pat. No. 4,871,717 disclose synthetic heptapeptide somatostatin analogues.

Coy et al., U.S. Pat. No. 4,904,642 disclose synthetic octapeptide somatostatin analogues.

Taylor et al., U.S. Pat. No. 5,073,541 disclose a method of treating small cell lung cancer.

Brady, European Patent Application No. 83111747.8 discloses dicyclic hexapeptide somatostatin analogues useful in the treatment of a number of human diseases.

Bauer et al., European Patent Application No. 85810617.2 disclose somatostatin derivatives useful in the treatment of a number of human diseases.

Eck and Moreau, European Patent Application No. 90302760.5 disclose therapeutic octapeptide somatostatin analogues.

Coy and Murphy, International Patent Application Serial No. PCT/US90/07074 disclose somatostatin analogues for therapeutic uses.

Schally et al., European Patent Application Serial No. EPA 911048445.2 disclose cyclic peptides for therapeutic use.

Bodgen and Moreau, International Patent Application Serial No. PCT/US92/01027 disclose compositions and methods for treating proliferative skin disease.

Somatostatin exerts it effects by binding to specific receptors expressed at the cell surface of cells comprising the central nervous system, the hypothalamus, the pancreas, and the gastrointestinal tract. These high-affinity somatostatin binding sites have been found to be abundantly expressed at the cell surface of most endocrine-active tumors arising from these tissues.

It is frequently clinically advantageous for a physician to be able to localize the site of pathological conditions in a Ala—Gly—Cys—Lys—Asn—Phe—Phe—Trp—Lys—Thr—Phe—Thr—Ser—Cys (SEQ ID NO.1)

(Single letter abbreviations for amino acids can be found in G. Zubay, *Biochemistry* (2d ed.), 1988, (MacMillan Publishing: New York), p.33). This peptide exerts a wide variety of biological effects in vivo. It is known to act physiologically on the central nervous system, the hypothalamus, the pancreas, and the gastrointestinal tract.

Somatostatin inhibits the release of insulin and glucagon from the pancreas, inhibits growth hormone release from the hypothalamus, and reduces gastric secretions. Thus, somatostatin has clinical and therapeutic applications for the alleviation of a number of ailments and diseases, both in humans and other animals. Native somatostatin is of limited utility, however, due to its short half-life in vivo, where it is rapidly degraded by peptidases. For this reason, somatostatin analogues having improved in vivo stability have been developed in the prior art.

Freidinger, U.S. Pat. No. 4,235,886 disclose cyclic hexapeptide somatostatin analogues useful in the treatment of a number of diseases in humans.

Coy and Murphy, U.S. Pat. No. 4,485,101 disclose synthetic dodecapeptide somatostatin analogues.

patient using non-invasive means. Such pathological conditions include diseases of the lungs, heart, liver, kidneys, bones and brain, as well as cancer, thrombosis, pulmonary embolism, infection, inflammation and atherosclerosis.

In the field of nuclear medicine, certain pathological conditions are localized, or their extent is assessed, by detecting the distribution of small quantities of internally-administered radioactively labeled tracer compounds (called radiotracers or radiopharmaceuticals). Methods for detecting these radiopharmaceuticals are known generally as imaging or radioimaging methods.

In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically *not* to localize at such pathological sites (termed negative contrast). In many situations it is a particular advantage to use a radiolabeled specific binding compound as a radiopharmaceutical which localizes specifically to the pathological site in vivo.

For example, expression of high-affinity binding sites for somatostatin is a marker for certain tumor cells, and specific binding with somatostatin can be exploited to locate and identify such tumor cells in vivo.

Methods for radiolabeling somatostatin analogues that have been modified so as to contain a tyrosine amino acid (Tyr or Y) are known in the prior art.

Albert et al., UK Patent Application 8927255.3 disclose radioimaging using somatostatin derivatives such as octreotide labeled with 123I.

Bakker et al., 1990, *J. Nucl. Med.* 31: 1501–1509 describe radioactive iodination of a somatostatin analog and its usefulness in detecting tumors in vivo.

Bakker et al., 1991, *J. Nucl. Med.* 32: 1184–1189 teach the usefulness of radiolabeled somatostatin for radioimaging in vivo.

Bomanji et al., 1992, *J. Nucl. Med.* 33: 1121–1124 describe the use of iodinated (Tyr-3) octreotide for imaging metastatic carcinoid tumors.

Alternatively, methods for radiolabeling somatostatin by covalently modifying the peptide to contain a radionuclide-chelating group have been disclosed in the prior art.

Albert et al., UK Patent Application 8927255.3 disclose radioimaging using somatostatin derivatives such as octreotide labeled with. $^{111}$In via a chelating group bound to the amino-terminus.

Albert et al., European Patent Application No. WO 91/01144 disclose radioimaging using radiolabeled peptides related to growth factors, hormones, interferons and cytokines and comprised of a specific recognition peptide covalently linked to a radionuclide chelating group.

Albert et al., European Patent Application No. 92810381.1 disclose somatostatin peptides having amino-terminally linked chelators.

Faglia et al., 1991, *J. Clin. Endocrinol. Metab.* 73: 850–856 describe the detection of somatostatin receptors in patients.

Kwekkeboom et al., 1991, *J. Nucl. Med.* 32: 981 Abstract #305 relates to radiolabeling somatostatin analogues with $^{111}$In.

Albert et al., 1991, Abstract LM10, 12th American Peptide Symposium: 1991 describe uses for $^{111}$In-labeled diethylene-triaminopentaacetic acid-derivatized somatostatin analogues.

Krenning et al., 1992, *J. Nucl. Med.* 33: 652–658 describe clinical scintigraphy using [$^{111}$In][DTPA]octreotide.

A variety of radionuclides are known to be useful for radioimaging, including $^{67}$Ga, $^{99m}$Tc (Tc-99m), $^{111}$In, $^{123}$I, $^{125}$I, $^{169}$Yb or $^{186}$Re. A number of factors must be considered for optimal radioimaging in humans. To maximize the efficiency of detection, a radionuclide that emits gamma energy in the 100 to 200 keV range is preferred. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site. Tc-99m is a preferred radionuclide because it emits gamma radiation at 140 keV, it has a physical half-life of 6 hours, and it is readily available on-site using a molybdenum-99/technetium-99m generator. Other radionuclides used in the prior art are less advantageous than Tc-99m. This can be because the physical half-life of such radionuclides are longer, resulting in a greater amount of absorbed radiation dose to the patient (e.g., indium- 111). Also, many disadvantageous radionuclides cannot be produced using an on-site generator.

Tc-99m is a transition metal that is advantageously chelated by a metal complexing moiety. Radiolabel complexing moieties capable of binding Tc-99m can be covalently linked to various specific binding compounds to provide a means for radiolabeling such specific binding compounds. This is because the most commonly available chemical species of Tc-99m, pertechnetate (TcO$_4^-$), cannot bind directly to most specific binding compounds strongly enough to be useful as a radiopharmaceutical. Complexing of Tc-99m with such radiolabel complexing moieties typically entails chemical reduction of the pertechnetate using a reducing agent such as stannous chloride.

The use of chelating agents for complexing Tc-99m is known in the prior art.

Byrne et al., U.S. Pat. No. 4,434,151 describe homocysteine containing chelating agents for Tc-99m.

Fritzberg, U.S. Pat. No. 4,444,690 describes a series of technetium-chelating agents based on 2,3-bis (mercaptoacetamido) propanoate.

Byrne et al., U.S. Pat. No. 4,571,430 describe homocysteine containing chelating agents for Tc-99m.

Byrne et al., U.S. Pat. No. 4,575,556 describe homocysteine containing chelating agents for Tc-99m.

Nosco et al., U.S. Pat. No. 4,925,650 describe Tc-99m chelating complexes.

Kondo et al., European Patent Application, Publication No. 483704 A1 disclose a process for preparing a Tc-99m complex with a mercapto-Gly-Gly-Gly moiety.

European Patent Application No. 84109831.2 describes bisamido, bisthiol Tc-99m ligands and salts thereof as renal function monitoring agents.

Davison et al., 1981, *Inorg. Chem.* 20: 1629–1632 disclose oxotechnetium chelate complexes.

Fritzberg et al., 1982, *J. Nucl. Med.* 23: 592–598 disclose a Tc-99m chelating agent based on N, N'-bis (mercaptoacetyl)-2,3-diaminopropanoate.

Byrne et al., 1983, *J. Nucl. Med.* 24: P126 describe homocysteine containing chelating agents for Tc-99m.

Bryson et al., 1988, *Inorg. Chem.* 27: 2154–2161 describe neutral complexes of technetium-99 which are unstable to excess ligand.

Misra et al., 1989, *Tet. Lett.* 30: 1885–1888 describe bisamine bisthiol compounds for radiolabeling purposes.

The use of chelating agents for radiolabeling specific-binding compounds is known in the art.

Gansow et al., U.S. Pat. No. 4,472,509 teach methods of manufacturing and purifying Tc-99m chelate-conjugated monoclonal antibodies.

Stavrianopoulos, U.S. Pat. No. 4,943,523 teach detectable molecules comprising metal chelating moieties.

Fritzberg et al., European Patent Application No. 86100360.6 describe dithiol, diamino, or diamidocarboxylic acid or amine complexes useful for making technetium-labeled imaging agents.

Albert et al., UK Patent Application 8927255.3 disclose radioimaging using somatostatin derivatives such as octreotide labeled with $^{111}$In via a chelating group bound to the amino-terminus.

Albert et al., European Patent Application No. WO 91/01144 disclose radioimaging using radiolabeled peptides related to growth factors, hormones, interferons and cytokines and comprised of a specific recognition peptide covalently linked to a radionuclide chelating group.

Fischman et al., International Patent Application, Publication No. WO93/13317 disclose chemotactic peptides attached to chelating moieties.

Kwekkeboom et al., 1991, *J. Nucl. Med.* 32: 981 Abstract #305 relates to radiolabeling somatostatin analogues with $^{111}$In.

Albert et al., 1991, Abstract LM10, 12th American Peptide Symposium: 1991 describe uses for $^{111}$In-labeled diethylene-triaminopentaacetic acid-derivatized somatostatin analogues.

Cox et al., 1991, Abstract, 7th International Symposium on Radiopharmacology, p. 16, disclose the use of, Tc-99m-, $^{131}$I- and $^{111}$In-labeled somatostatin analogues in radiolocalization of endocrine tumors in vivo by scintigraphy.

Methods for labeling certain specific-binding compounds with Tc-99m are known in the prior art.

Hnatowich, U.S. Pat. No. 4,668,503 describe Tc-99m protein radiolabeling.

Tolman, U.S. Pat. No. 4,732,684 describe conjugation of targeting molecules and fragments of metallothionein.

Nicolotti et al., U.S. Pat. No. 4,861,869 describe bifunctional coupling agents useful in forming conjugates with biological molecules such as antibodies.

Fritzberg et al., U.S. Pat. No. 4,965,392 describe various S-protected mercaptoacetylglycylglycine-based chelators for labeling proteins.

Schochat et al., U.S. Pat. No. 5,061,641 disclose direct radiolabeling of proteins comprised of at least one "pendent" sulfhydryl group.

Fritzberg et al., U.S. Pat. No. 5,091,514 describe various S-protected mercaptoacetylglycylglycine-based chelators for labeling proteins.

Gustavson et al., U.S. Pat. No. 5,112,953 disclose Tc-99m chelating agents for radiolabeling proteins.

Kasina et al., U.S. Pat. No. 5,175,257 describe various combinations of targeting molecules and Tc-99m chelating groups.

Dean et al., U.S. Pat. No. 5,180,816 disclose methods for radiolabeling a protein with Tc-99m via a bifunctional chelating agent.

Sundrehagen, International Patent Application, Publication No. WO85/03231 disclose Tc-99m labeling of proteins.

Reno and Bottino, European Patent Application 87300426.1 disclose radiolabeling antibodies with Tc-99m.

Bremer et al., European Patent Application No. 87118142.6 disclose Tc-99m radiolabeling of antibody molecules.

Pak et al., European Patent Application No. WO 88/07382 disclose a method for labeling antibodies with Tc-99m.

Goedemans et al., PCT Application No. WO 89/07456 describe radiolabeling proteins using cyclic thiol compounds, particularly 2-iminothiolane and derivatives.

Dean et al., International Patent Application, Publication No. WO89/12625 teach bifunctional coupling agents for Tc-99m labeling of proteins.

Schoemaker et al., International Patent Application, Publication No. WO90/06323 disclose chimeric proteins comprising a metal-binding region.

Thornback et al., EPC Application No. 90402206.8 describe preparation and use of radiolabeled proteins or peptides using thiol-containing compounds, particularly 2-iminothiolane.

Gustavson et al., International Patent Application, Publication No. WO91/09876 disclose Tc-99m chelating agents for radiolabeling proteins.

Rhodes, 1974, *Sem. Nucl. Med.* 4: 281–293 teach the labeling of human serum albumin with technetium-99m.

Khaw et al., 1982, *J. Nucl. Med.* 23: 1011–1019 disclose methods for labeling biologically active macromolecules with Tc-99m.

Schwartz et al., 1991, *Bioconjugate Chem.* 2: 333 describe a method for labeling proteins with Tc-99m using a hydrazinonicotinamide group.

Attempts at radiolabeling peptides have been reported in the prior art.

Ege et al., U.S. Pat. No. 4,832,940 teach radiolabeled peptides for imaging localized T-lymphocytes.

Morgan et al., U.S. Pat. No. 4,986,979 disclose methods for imaging sites of inflammation.

Flanagan et al., U.S. Pat. No. 5,248,764 describe conjugates between a radiolabel chelating moiety and atrial natiuretic factor-derived peptides.

Ranby et al., 1988, PCT/US88/02276 disclose a method for detecting fibrin deposits in an animal comprising covalently binding a radiolabeled compound to fibrin.

Lees et al., 1989, PCT/US89/01854 teach radiolabeled peptides for arterial imaging.

Morgan et al., International Patent Application, Publication No. WO90/10463 disclose methods for imaging sites of inflammation.

Flanagan et al., European Patent Application No. 90306428.5 disclose Tc-99m labeling of synthetic peptide fragments via a set of organic chelating molecules.

Stuttle, PCT Application, Publication No. WO 90/15818 describes Tc-99m labeling of RGD-containing oligopeptides.

Rodwell et al., 1991, PCT/US91/03116 disclose conjugates of "molecular recognition units" with "effector domains".

Cox, International Patent Application No. PCT/US92/04559 discloses radiolabeled somatostatin derivatives containing two cysteine residues.

Rhodes et al., International Patent Application, Publication No. WO93/12819 teach peptides comprising metal ion-binding domains.

Lyle et al, International Patent Application, Publication No. WO93/15770 disclose Tc-99m chelators and peptides labeled with Tc-99m.

Coughlin et al, International Patent Application, Publication No. WO93/21151 disclose bifunctional chelating agents comprising thiourea groups for radiolabelingtargeting molecules.

Knight et al., 1990, 37th Annual Meeting of the Society of Nuclear Medicine, Abstract #209, claim thrombus imaging using Tc-99m labeled peptides.

Babich et al., 1993, *J. Nucl. Med.* 34: 1964–1974 describe Tc-99m labeled peptides comprising hydrazinonicotinamide derivatives.

Methods for directly labeling somatostatin, derivatives of somatostatin, analogues of somatostatin or peptides that bind to the somatostatin receptor and contain at least 2 cysteine residues that form a disulfide or wherein the disulfide is reduced to the sulfhydryl form, are disclosed in co-owned U.S. Pat. No. 5,225,180, issued Jul. 6, 1993 which is hereby incorporated by reference in its entirety.

The use of chelating agents for radiolabeling peptides, and methods for labeling peptides with Tc-99m are known in the prior art and are disclosed in co-pending U.S. patent applications Ser. Nos. 07/653,012, 07/807,062, 07/871,282, 07/893,981, 07/955,466, 08/092,355, and 08/095,760.

There remains a need for synthetic (to make routine manufacture practicable and to ease regulatory acceptance) somatostatin analogues having increased in vivo stability, to be used therapeutically, as scintigraphic agents when radiolabeled with Tc-99m or other detectable radioisotopes for use in imaging tumors in vivo, and as radiotherapeutic agents when radiolabeled with a cytotoxic radioisotope such as rhenium-188. Small synthetic somatostatin analogues are provided by this invention that specifically fulfill this need.

SUMMARY OF THE INVENTION

The present invention provides somatostatin analogues that comprise cyclic peptides for therapeutic applications, including radiotherapeutic applications, and diagnostic applications, including radiodiagnostic applications, in particular scintigraphic imaging applications. Distinct from native somatostatin, the cyclic peptides of the invention are not comprised of a disulfide bond. The invention also provides cyclic peptide reagents comprised of cyclic peptide somatostatin analogues wherein such peptides incorporate a covalently linked metal ion-binding moiety. The invention provides such cyclic peptides, cyclic peptide reagents and radiolabeled cyclic peptide reagents that are scintigraphic imaging agents, radiodiagnostic agents and radiotherapeutic agents. Scintigraphic imaging agents of the invention comprise cyclic peptide reagents radiolabeled with a radioisotope, preferably technetium-99m. Radiotherapeutic agents of the invention comprise cyclic peptide reagents radiolabeled with a cytotoxic radioisotope, preferably rhenium-186 or rhenium-188. Methods for making and using such cyclic peptides, cyclic peptide reagents and radiolabeled embodiments thereof are also provided.

The invention provides compositions of matter comprising a specific binding peptide that specifically binds to somatostatin receptors in a mammalian body, covalently linked to a metal ion-complexing moiety. The compositions of matter of the invention have formula:

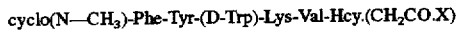

wherein X is (amino acid)$_n$-B-(amino acid)$_m$-Z, wherein B is is a thiol-containing moiety that is cysteine, homocysteine, isocysteine, or penicillamine; (amino acid)$_n$ and (amino acid)$_m$ are each independently any primary α- or β-amino acid that does not comprise a thiol group; Z is —OH or —NH$_2$; and n and m are each independently an integer between 2 and 5 and 0 and 5, respectively.

In the formulae describing the compositions of matter of the invention, the combination of the term "cyclo" and an underlined amino acid sequence will be understood to mean that the underlined amino acid sequence is cyclized through a peptide bond linking the amino terminus of the first amino acid of the sequence to the carboxyl terminus of the last amino acid of the sequence. When followed by a parenthetical term such as "(CH$_2$CO.X), said parenthetical term will be understood to mean that the sequence in parentheses is covalently linked to the amino acid sidechain sulfur atom of the thiol-containing amino acid in the underlined amino acid sequence, forming a sulfide bond therewith. Thus, in the above chemical structure, it will be understood that the —CH$_2$CO.X group is covalently linked to the sidechain sulfur atom of homocysteine. An example of such a chemical formula is shown in Example 2.

A preferred embodiment of the compositions of matter of the invention is a compound having formula:

The compositions of matter of the invention have utility for a number of diagnostic and therapeutic purposes.

Thus, one aspect of the invention provides reagents for preparing radiolabeled scintigraphic imaging agents for imaging sites within a mammalian body having an overabundance of somatostatin receptors. In such embodiments, the metal ion-complexing moiety comprises a radiolabel binding moiety, and the reagent forms a complex with the radiolabel via complex formation with said moiety. In one embodiment of this aspect of the invention, the scintigraphic imaging agent is formed by complexing the reagent with Tc-99m under reducing conditions.

Thus, the invention also comprises scintigraphic imaging agents that are complexes of the reagents of the invention with Tc-99m and methods for radiolabeling the reagents. Tc-99m radiolabeled complexes provided by the invention are formed by reacting the reagents of the invention with Tc-99m in the presence of a reducing agent. Preferred reducing agents include but are not limited to dithionite ion, stannous ion and ferrous ion. Complexes of the invention are also formed by labeling the reagents of the invention with Tc-99m by ligand exchange of a prereduced Tc-99m complex as provided herein.

A preferred embodiment of the reagents provided by the invention for preparing scintigraphic imaging agents is a compound having formula:

Preferred imaging agents comprise Tc-99m complexes of this reagent.

The invention also provides kits for preparing scintigraphic imaging agents that are the reagents of the invention radiolabeled with Tc-99m. Kits for labeling the reagents provided by the invention with Tc-99m are comprised of a sealed vial containing a predetermined quantity of a reagent of the invention and a sufficient amount of reducing agent to label the reagent with Tc-99m.

In a second aspect of the invention are provided imaging agents wherein the compositions of matter of the invention are radiolabeled with a radioisotope of iodine, preferably I-123, I-125, or I-131. The invention provides radioiodinated imaging agents that are complexes of the reagents of the invention with radiolabeled iodine.

A preferred embodiment of the reagents provided by the invention for preparing radioiodinated imaging agents is a compound having formula:

Preferred imaging agents comprise radioiodinated embodiments of this reagent.

In a third aspect are provided nonradioactively-labeled imaging agents, comprising reagents that are the compositions of matter of the invention complexed with a paramagnetic metal ion or particle. In embodiments of this aspect of the invention, the paramagnetic metal ion is complexed with the metal ion-complexing moiety. In embodiments where a particle, preferably a superparamagnetic metal particle, is used, the compositions of matter of the invention are linked to the superparamagnetic particle either covalently or associatively using methods described by Weissleder et al. (1992, Radiology 182: 381–385). The invention provides such imaging agents for use in magnetic resonance imaging. Methods for preparing these non-radiolabeled imaging agents are also provided.

A preferred embodiment of the reagents provided by the invention for preparing such non-radioactively-labeled imaging agents is a compound having formula:

Preferred non-radioactively labeled imaging agents comprise ferric ion complexes of this reagent.

Therapeutic agents are also provided herein. In a fourth aspect, the invention provides the compositions of matter of the invention uncomplexed with a metal ion as a therapeutic agent per se. Preferred embodiments of such therapeutic agents provided by the invention are compounds having formula:

In a fifth aspect, the invention provides radiolabeled therapeutic agents comprising a reagent for preparing the therapeutic agent that is a composition of matter provided by the invention. In such embodiments, the compositions of matter of the invention are provided wherein the metal ion-complexing moiety is complexed with a β-particle emitting or a conversion electron emitting radioisotope. Preferred embodiments of β-particle emitting radioisotopes are rhenium-186 and rhenium-188. A preferred conversion electron emitting radioisotope is tin-117m. The invention provides such radioisotope complexes of the compositions of matter of the invention for radiotherapeutic treatment of somatostatin-receptor expressing pathological cells and tissues, particularly neoplastic and metastatic cells. Methods for preparing such therapeutic radioisotope complexes of the compositions of matter of the invention are also provided.

A preferred embodiment of the reagents of the invention provided for preparing such radiotherapeutic agents is a compound having formula:

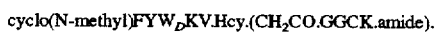

cyclo(N-methyl)FYW$_D$KV.Hcy.(CH$_2$CO.GGCK.amide).

Preferred radiotherapeutic agents comprise β-particle emitting or conversion electron-emitting metal ion complexes with this reagent.

In another aspect of the radiotherapeutic agents of the invention are provided radiotherapeutic agents wherein the compositions of matter of the invention are radiolabeled with a radioisotope of iodine, preferably I-125 or I-131, or with astatine-211. The invention also provides the radiolabeled therapeutic agents themselves, as well as methods for radiolabeling the reagents.

Preferred embodiments of the reagents of the invention provided for preparing these therapeutic radioiodinated and radioastatinated agents are compounds having formula:

cyclo(N-methyl)FYW$_D$KV.Hcy.(CH$_2$CO.GGCK.amide).

Preferred radiotherapeutic agents comprise radioiodinated and radioastatinated embodiments of this reagent.

Therapeutic agents are provided that are nonradioactively-labeled, metal atom- complexed agents, comprising reagents that are the compositions of matter of the invention complexed with a nonradioactive metal atom, such as copper, zinc or rhenium. In embodiments of this aspect of the invention, the nonradioactive metal ion is complexed with the metal ion-complexing moiety. The invention provides such therapeutic agents for use in treating conditions in which somatostatin receptors are overexpressed in the cells comprising certain tissues, and in treating neoplastic cells which hyperexpress somatostatin receptors. Methods for preparing these non-radiolabeled metal atom complexed therapeutic agents are also provided.

A preferred embodiment of the reagents of the invention provided for preparing non- radioactively-labeled therapeutic agents is a compound having formula:

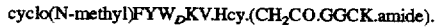

cyclo(N-methyl)FYW$_D$KV.Hcy.(CH$_2$CO.GGCK.amide).

Preferred non-radioactively labeled therapeutic agents comprise a rhenium complex of this reagent.

This invention provides methods for preparing peptide embodiments of the reagents of the invention by chemical synthesis in vitro. In a preferred embodiment, peptides are synthesized by solid phase peptide synthesis.

This invention provides methods for using the diagnostic and radiodiagnostic and therapeutic and radiotherpaeutic agents of the invention. For radiolabeled embodiments of the agents of the invention, for example, Tc-99m labeled scintigraphic imaging agents, an effective diagnostic or therapeutic amount of the diagnostic or radiodiagnostic or therapeutic or radiotherapeutic agent of the invention are administered. In radiodiagnostic embodiments, localization of the radiolabel is detected using conventional methodologies such as gamma scintigraphy. In non-radioactive diagnostic embodiments, localization of sites of accumulation of the paramagnetic metal-labeled diagnostic agents of the invention is achieved using magnetic resonance imaging methodologies. The imaging agents provided by the invention have utility for tumor imaging, particularly for imaging primary and metastatic neoplastic sites wherein said neoplastic cells express somatostatin receptors (SSTR), and in particular such primary and especially metastatic tumor cells that have been clinically recalcitrant to detection using conventional methodologies. In addition, the imaging agents of the invention are useful in detecting sites of T lymphocyte accumulation associated with occult disease or pathology, e.g., as occurs in patients suffering from tuberculosis.

The invention provides methods for using the somatostatin analogues of the invention to alleviate diseases or other ailments in animals, preferably humans. These diseases and ailments include but are not limited to diabetes and diabetes-related retinopathy, cirrhosis of the liver and hepatitis infection, bleeding ulcers and other gastrointestinal bleeding, pancreatitis, central nervous system disorders, endocrine disorders, Alzheimer's disease, acromegaly and other diseases and disorders related to the production of inappropriate levels of growth hormone in vivo, and cancer, particularly those cancers whose growth is dependent or influenced by growth hormone production. Non-radiolabeled therapeutic embodiments also have utility for treating SSTR hyperexpression-related ailments, such as diarrhea cause by SSTR-hyperexpressing gastrinoma. Dosages of the somatostatin analogues provided by the invention may be the same as those dosages of native somatostatin routinely used for treatment of the above or other diseases, or less of the compounds of the invention may be administered due to their longer in vivo half-life.

Therapeutic uses also include radiotherapeutic ablation of neoplastic and metastatic malignant cells in patients bearing tumors the cells of which express the somatostain receptor. Use of the radiotherapeutic agents of the invention includes primary therapeutic use for tumors recalcitrant to more conventional therapies and for tumors that are inoperable, as well as adjunct therapies supplemental to surgery, radiation therapy or conventional chemotherapy.

The radiolabeled embodiments of the invention also have utility as surgical guides for identifying somatostatin receptor-expressing tumor tissue during surgery. For such use in radioisotope guided surgery, malignant tissue otherwise invisible to the surgeon can be recognized and excised during otherwise conventional surgery.

Specific preferred embodiments of the present invention will become evident from the following more detailed description of certain preferred embodiments and the claims.

DETAILED DESCRIPTION OF PREFERRED EMBODIMENTS

Figure 1:
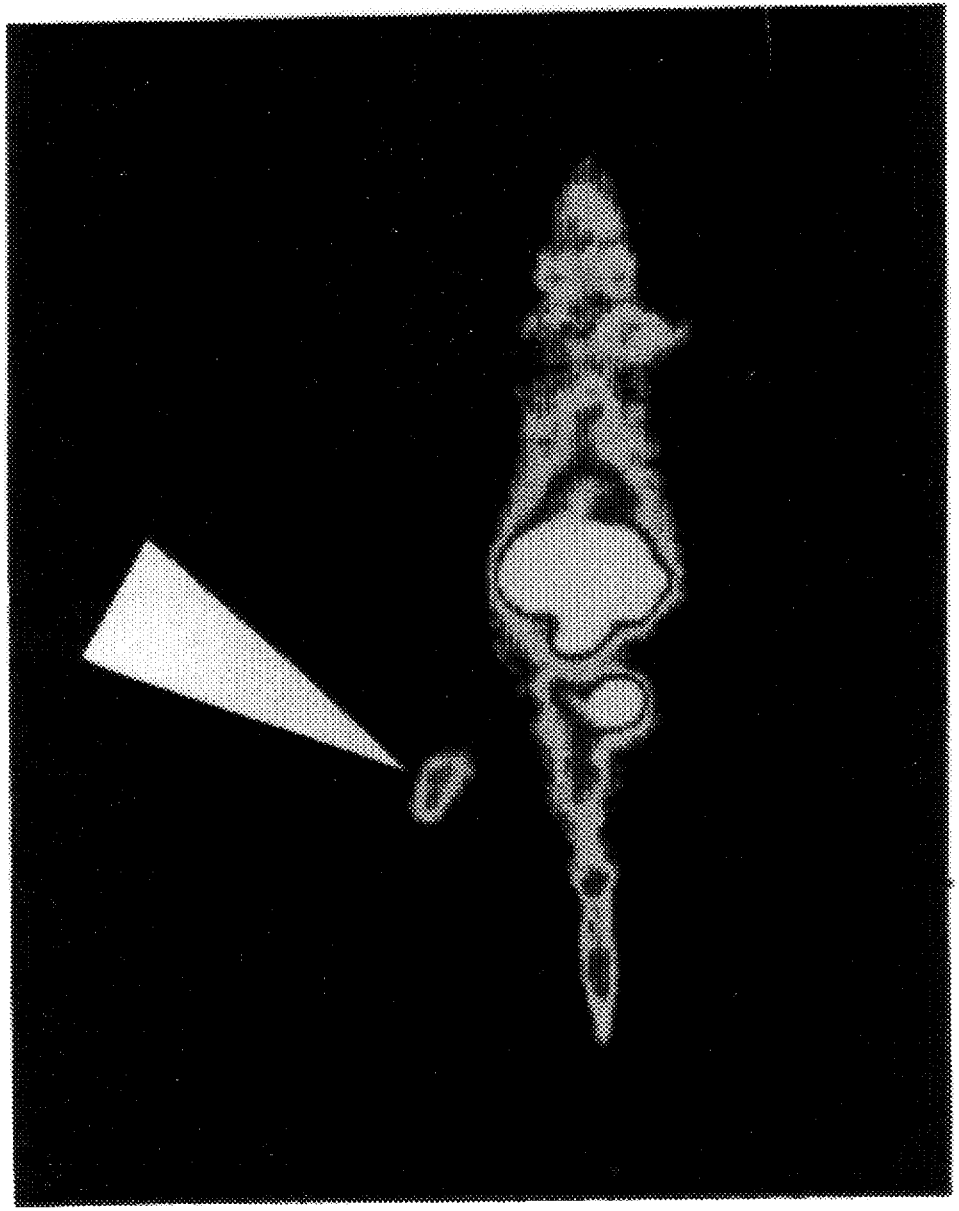
FIG. 1 shows an image of $^{99m}$Tc-labeled P587 in a tumor-bearing rat, indicated by an arrow, showing high uptake at the tumor site in the lower leg.

The present invention provides cyclic peptides that are somatostatin analogues and that do not comprise of a disulfide bond. Such somatostatin analogues thereby possess increased in vivo stability compared with native somatostatin. These cyclic peptides are themselves therapeutic agents for alleviating diseases and other ailments in animals including humans.

Also provided by the invention are cyclic peptides that may be radioiodinated or radioastatinated and which are thereby useful in radiotherapeutic and radiodiagnostic applications.

Another embodiment of these cyclic peptides that is provided by this invention are cyclic peptide reagents wherein the cyclic peptides of the invention are covalently linked to a metal ion-complexing moiety. Such cyclic peptide reagents are capable of being radiolabeled to provide radiodiagnostic or radiotherapeutic agents. One example of a radiodiagnostic application using the radiolabeled agents of the invention is scintigraphic imaging, wherein the location and extent of somatostatin receptor-bearing tumors may be determined. The cyclic peptide reagents of the invention can also advantageously be radiolabeled with cytotoxic radioisotopes such as rhenium-186 or rhenium-188 for radiotherapeutic uses. The cyclic peptide reagents of the invention are also useful in preparing complexes with non-radioactive metals, said complexes being useful therapeutically.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Other radionuclides may also be used in the practice of the invention as disclosed herein.

The term scintigraphic imaging agent as used herein is meant to encompass a radiolabeled agent capable of being detected with a radioactivity detecting means (including but not limited to a gamma-camera, a Geiger-Muller counter and a scintillation detector probe).

Radiotherapeutic embodiments of the invention, on the other hand, are advantageously labeled with a cytotoxic radioisotope, including but not limited to copper-67, iodine-125, iodine-131, rhenium-186, rhenium-188, and astatine-211, most preferably $^{186}$Re or $^{188}$Re. Such embodiments are useful in the treatment of somatostatin-related diseases or other ailments in animals, preferably humans, including but not limited to cancer and other diseases characterized by the growth of malignant or benign tumors capable of binding somatostatin or somatostatin analogues via the expression of somatostatin receptors on the cell surface of cells comprising such tumors.

The present invention provides reagents for preparing diagnostic and radiodiagnostic agents, and therapeutic and radiotherapeutic agents. The reagents provided by the invention comprise a metal ion-complexing moiety covalently linked to a specific binding peptide that binds to somatostatin receptor sites within a mammalian body.

Small compounds, preferably having a molecular weight of less than 10,000 daltons, are of distinct commercial advantage. Such small compounds can be readily manufactured. Moreover, they are likely not to be immunogenic and to clear rapidly from the vasculature, thus allowing for better and more rapid imaging. In contrast, larger molecules such as antibodies or fragments thereof, or other biologically-derived peptides larger than 10,000 daltons, are costly to manufacture, and are likely to be immunogenic and clear more slowly from the bloodstream, thereby interfering with rapid diagnoses in vivo.

It is an advantage of the somatostatin analogues provided by this invention that the non-disulfide cyclic linkage contained therein is stable under the conditions of radiolabeling the covalently linked radiolabel-binding moiety. In contrast, for example, Tc-99m conjugation to a Tc-99m binding moiety covalently linked to native somatostatin, or to a somatostatin analogue having a disulfide bond, can result in reduction of the disulfide accompanied by a loss of biological activity. Such loss of biological activity can also occur in vivo using native somatostatin, or to any somatostatin analogue having a disulfide bond. The present invention is not subject to similar losses in biological activity in vivo because the non-disulfide cyclic linkages in each of the somatostatin analogues of the invention comprise stable covalent bonds.

For purposes of this invention, the term "specific binding peptide" is intended to mean any peptide compound that specifically binds to a target site in a mammalian body defined by an overabundance of somatostatin receptor (SSTR) molecules. "Specific binding" will be understood by those with skill in this art as meaning that the peptide localizes to a greater extent at the target site that to surrounding tissues. Such specific binding is advantageous in diagnostic imaging agents comprising such specific binding peptides because they are dispersed throughout a mammalian body after administration and such specific localization of reagent-bound radioactivity provides visual definition of the target in vivo.

Each specific-binding peptide-containing embodiment of the invention is comprised of a sequence of amino acids. The term amino acid as used in this invention is intended to include all L- and D-, primary α- and β-amino acids, naturally occurring, modified, substituted, altered and otherwise. Specific binding peptide embodiments of the reagents of the invention comprise specific binding peptides having a molecular weight of less than about 5,000 daltons. Particularly preferred embodiments of the specific binding peptides of the invention include peptides that bind specifically and with high affinity to the somatostatin receptor (SSTR) on SSTR-expresing cells, particularly tumor cells and activated T-lymphocyte cells. Reagents comprising specific-binding peptides provided by the invention include but are not limited to reagents comprising peptides having the following amino acid sequences (the amino acids in the following peptides are L-amino acids except where otherwise indicated):

cyclo(N-methyl)FYW$_D$KV.Hcy.(CH$_2$CO.GGC.amide)
cyclo(N-methyl)FYW$_D$KV.Hcy.(CH$_2$CO.GGCK.amide)
cyclo(N-methyl)FYW$_D$KV.Hcy.(CH$_2$CO.GGCR.amide)
cyclo(N-methyl)FYW$_D$KV.Hcy.(CH$_2$CO.GGCRD.amide)
cyclo(N-methyl)FYW$_D$KV.Hcy.(CH$_2$CO.GGCRK.amide)
cyclo(N-methyl)FYW$_D$KV.Hcy.(CH$_2$CO.GGCRR.amide)
cyclo(N-methyl)FYW$_D$KV.Hcy.(CH$_2$CO.GGCKK.amide)
cyclo(N-methyl)FYW$_D$KV.Hcy.(CH$_2$CO.GGCKKK.amide)
cyclo(N-methyl)FYW$_D$KV.Hcy.(CH$_2$CO.GGC.Orn.amide)
cyclo(N-methyl)FYW$_D$KV.Hcy.(CH$_2$CO.GGCKDK.amide)
cyclo(N-methyl)FYW$_D$KV.Hcy.(CH$_2$CO.GGC.Orn.D.Orn.amide)
cyclo(N-methyl)FYW$_D$KV.Hcy.(CH$_2$CO.GGC.Orn.D.amide)
cyclo(N-methyl)FYW$_D$KV.Hcy.(CH$_2$CO.KKC.amide)
cyclo(N-methyl)FYW$_D$KV.Hcy.(CH$_2$CO.KRC.amide)
cyclo(N-methyl)FYW$_D$KV.Hcy.(CH$_2$CO.RRC.amide)
cyclo(N-methyl)FYW$_D$KV.Hcy.(CH$_2$CO.KKCK.amide)
cyclo(N-methyl)FYW$_D$KV.Hcy.(CH$_2$CO.GRCK.amide)
cyclo(N-methyl)FYW$_D$KV.Hcy.(CH$_2$CO.KCR.amide).

(Single-letter abbreviations for amino acids can be found in Zubay, ibid., p.33; other abbreviations are as in the Legend to Table I). This list of reagents provided by the invention is illustrative and not intended to be limiting or exclusive, and it will be understood by those with skill in the art that reagents comprising combinations of the peptides disclosed herein or their equivalents may be covalently linked to any of the chelating moieties of the invention and be within its scope.

In a preferred embodiment, the reagent of the invention has formula:

Technetium-99m labeled scintigraphic imaging agents according to the present invention can be prepared by the addition of an appropriate amount of Tc-99m or Tc-99m complex into the vials and reaction under conditions described in Example 3 hereinbelow. The kit may also contain conventional pharmaceutical adjunct materials such as, for example, pharmaceutically acceptable salts to adjust the osmotic pressure, buffers, preservatives and the like. The

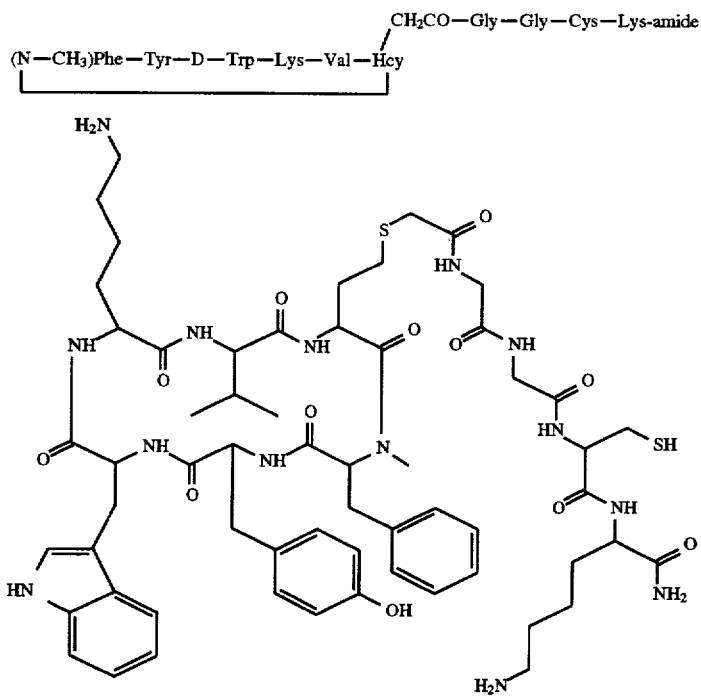

Specific-binding peptides comprising the reagents of the present invention can be chemically synthesized in vitro. Such peptides can generally advantageously be prepared on a peptide synthesizer. The peptides of this invention can be synthesized wherein the metal ion-complexing moiety is covalently linked to the peptide during chemical synthesis in vitro, using techniques taught herein (see, for example, Example 2, subsection O).

In scintigraphic imaging embodiments of the invention, a complex of technetium-99m is formed with the reagents of this invention. To accomplish this, Tc-99m, preferably as a salt of Tc-99m pertechnetate, is reacted with the reagents of this invention in the presence of a reducing agent. Preferred reducing agents are dithionite, stannous and ferrous ions; the most preferred reducing agent is a stannous salt such as stannous chloride. In an additional preferred embodiment, the reducing agent is a solid-phase reducing agent. Complexes and means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a reagent of this invention with a pre-formed labile complex of technetium and another compound known as a transfer ligand (such as tartrate, citrate, gluconate or mannitol, for example). This process is known as ligand exchange and is well known to those skilled in the art. Among the Tc-99m pertechnetate salts useful with the present invention are included the alkali metal salts such as the sodium salt, or ammonium salts or lower alkyl ammonium salts.

components of the kit may be in liquid, frozen or dry form. In a preferred embodiment, kit components are provided in lyophilized form. Radiolabeled scintigraphic imaging reagents according to the present invention may be prepared by reaction under conditions described in Example 3 hereinbelow.

Radioactively labeled reagents provided by the present invention are provided having a suitable amount of radioactivity. In forming, for example, Tc-99m radioactive complexes, it is generally preferred to form radioactive complexes in solutions containing radioactivity at concentrations of from about 0.01 millicurie (mCi) to 100 mCi per mL.

The imaging reagents provided by the present invention can be used for visualizing organs such as the kidney for diagnosing disorders in these organs, and tumors, in particular gastrointestinal tumors, myelomas, small cell lung carcinoma and other APUDomas, endocrine tumors such as medullary thyroid carcinomas and pituitary tumors, brain tumors such as meningiomas and astrocytomas, and tumors of the prostate, breast, colon, and ovaries can also be imaged. In accordance with this invention, the Tc-99m labeled peptide reagents are administered in a single unit injectable dose. The Tc-99m labeled peptide reagents provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The somatostatin receptor-binding cyclic peptides and non-radioactive metal complexes of the cyclic peptide reagents of the invention may be used clinically as therapeutic agents to promote regression of certain types of tumors, particularly those that express somatostatin receptors. The somatostatin analogue cyclic peptides of the invention can also be used to reduce the hormonal hypersecretion that often accompanies certain cancers, such as the APU-Domas. Peptides of the invention used as therapeutic agents may be administered by any appropriate route, including intravenous, intramuscular or by mouth, and in any acceptable pharmaceutical carrier, in doses ranging from about 0.1 to about 49 mg/kg body weight/day.

This invention also provides peptides radiolabled with cytotoxic radioisotopes such as rhenium-186 or rhenium-188 that may be used for radiotherapy of certain tumors as described above. For this purpose, an amount of radioactive isotope from about 10mCi to about 200mCi may be administered via any suitable clinical route, preferably by intravenous injection.

The methods for making and labeling these compounds are more fully illustrated in the following Examples. These Examples illustrate certain aspects of the above-described method and advantageous results, and are shown by way of illustration and not limitation.

EXAMPLE 1

Solid Phase Peptide Synthesis

Solid phase peptide synthesis (SPPS) was carried out on a 0.25 millimole (mmole) scale using an Applied Biosystems Model 431 A Peptide Synthesizer and using 9-fluorenylmethyloxycarbonyl (Fmoc) amino-terminus protection, coupling with dicyclohexyl-carbodiimide/ hydroxybenzotriazole or 2-(1 H-benzo-triazol-1-yl)-1,1,3,3-tetramethyluronium hexafluorophosphate/ hydroxybenzotriazole (HBTU/HOBT), and using p-hydroxymethyl-phenoxymethylpolystyrene (HMP) or Sasrin™ resin for carboxyl-terminus acids or Rink amide resin for carboxyl-terminus amides.

Fmoc.Hcy(S-trityl) and Fmoc.Pen(S-trityl) were prepared from the appropriate amino acid by tritylation with triphenylmethanol in trifluoroacetic acid, followed by Fmoc derivitization as described by Atherton et al. (1989, *Solid Phase Peptide Synthesis*, IRL Press: Oxford) and further in Example 2, subsection J below. Fmoc-S-(3-Boc-aminopropyl) cysteine was prepared from L-cysteine and Boc-aminopropyl bromide in methanolic sodium methoxide followed by treatment with O-9-fluorenylmethyl-O'-N-succcinimidyl carbonate (FmocOSu) at pH 10.

2-haloacetyl groups were introduced either by using the appropriate 2-haloacetic acid as the last residue to be coupled during SPPS or by treating the N-terminus free amino peptide bound to the resin with either 2-haloacetic acid/ diisopropylcarbodiimide/N-hydroxysuccinimide in NMP of 2-haloacetic anhydride/ diisopropylethylamine in NMP.

Thiol-containing peptides were reacted with chloroacetyl-containing, thiol-protected Tc-99m complexing moieties at pH 10 for 0.5–24 hours at room temperature, optionally followed by acetic acid acidification and evaporation of the solution to give the corresponding peptide-sulfide adduct, as described in more detail in Example 2, subsection O below. Deprotection and purification were routinely performed as described to yield the chelator-peptide conjugate.

Sasrin™ resin-bound peptides were cleaved using a solution of 1% TFA in dichloromethane to yield the protected peptide.

Where appropriate, protected peptide precursors were cyclized between the amino- and carboxyl-termini by reaction of sidechain-protected, amino-terminal free amine and carboxyl-terminal free acid using diphenylphosphorylazide, as described in more detail in Example 2, subsection M below.

HMP or Rink amide resin-bound products were routinely cleaved and protected cyclized peptides deprotected using a solution comprised of trifluoroacetic acid (TFA), or TFA and methylene chloride, optionally comprising water, thioanisole, ethanedithiol, and triisopropylsilane in ratios of 100:5:5:2.5:2, for 0.5–3 hours at room temperature. Where appropriate, products were re-S-tritylated in triphenolmethanol/TFA, and N-Boc groups re-introduced into the peptide using $(Boc)_2O$.

Crude peptides were purified by preparative high pressure liquid chromatography (HPLC) using a Waters Delta-Pak C18 column and gradient elution with 0.1% TFA in water modified with acetonitrile. After column elution, acetonitrile was evaporated from the eluted fractions, which were then lyophilized. The identity of each product so produced and purified was confirmed by fast atom bombardment mass spectroscopy (FABMS) or electrospray mass spectroscopy (ESMS).

EXAMPLE 2

Synthesis of cyclo(N-$CH_3$)phenylalanyl-tyrosyl-Dtryptophvl-lysyl-valyl-homocysteine, S-2-acetyl-glycyl-glycyl-cysteinyl-lysinamide (P587)

A. Synthesis of N-α-carbobenzoxy-N-ε-tert-butoxycarbonyl-lysine, N-hydroxy-succinimide ester To a mixture of N-αe-carbobenzoxy-N-ε-tert-butoxycarbonyl lysine (23 g, 60.5 mmol) and N-hydroxysuccinimide (7.1 g, 61.7 mmol) in 180 mL dry tetrahydrofuran (THF) cooled in a cold water bath was added diisopropylcarbodiimide (9.66 mL, 61.7 mmol). This reaction mixture was stirred overnight and then filtered and the filtrate evaporated. The residue of the filtrate was then redissolved in minimal ethyl acetate, 200 mL ether and 200 mL hexanes. The title compound precipitated from this mixture and was recovered by filtration, washed with cold hexanes and dried to give 28.1 g (58.9 mmol, 97% yield).

B. Synthesis of N-α-carbobenzoxy-N-ε-tert-butoxycarbonyl-lysyl-valine, methyl ester To a solution of valine methyl ester (8.38 g, 50 mmol) and diisopropylethylamine (12.7 mL, 50 mmol) in 150 mL THF was added N-α-carbobenzoxy-N-ε-tert-butoxycarbonyl lysine, N-hydroxysuccinimide ester (23.9 g, 50 mmol), followed by an additional 50 mL THF. After 2 h the solvent was removed by evaporation and 50 mL ethyl acetate added to the residue. This solution was washed sequentially with 200 mL 5 % citric acid, 200 mL saturated sodium bicarbonate and 200 mL saturated brine, dried over anhydrous magnesium sulfate, filtered and evaporated. The resulting oil was dissolved in minimal ethyl acetate, 200 mL ether and 200 mL hexanes. The title compound was isolated by filtration and dried to yield 20 g (40.5 mmol, 81% yield).

C. Synthesis of N-ε-tert-butoxycarbonyl-lysyl-valine, methyl ester

To a solution of N-α-carbobenzoxy-N-ε-tert-butoxycarbonyl-lysyl-valine, methyl ester (19 g, 38.5 mmol) and acetic acid (1 mL) in 100 mL ethyl acetate was added 10% palladium on carbon catalyst (0.19 g) and stirred under a hydrogen atmosphere overnight. The reaction mixture was then filtered over Celite, the filtrate evaporated and the residue redissolved in 100 mL methanol containing 1mL acetic acid. To this solution was added 10% palladium on carbon (0.19 g) and the mixture was hydrogenated under a pressure of 45 pounds per square inch for 2 h using a Parr hydrogenator. The reaction mixture was again filtered over Celite and the filtrate evaporated to give 13.56 g of the title compound (37.7 mmol, 98% yield).

D. Synthesis of fluorenylmethoxycarbonyl-D-tryptophan, N-hydroxysuccinimide ester To a solution of N-α-fluorenylmethoxycarbonyl-tryptophan hemihydrate (25 g, 82.1 mmol) and N-hydroxysuccinimide (9.78 g, 85 mmol) in 250 mL dry THF cooled in a cold water bath was added diisopropylcarbodiimide (13.3 mL, 85 mmol). The reaction mixture was stirred overnight, filtered and the filtrate evaporated. The residue was then redissolved in toluene and hexanes. The title compound was isolated by filtration and dried to yield 34 g (66.5 mmol, 81% yield).

E. Synthesis of fluorenylmethoxycarbonyl-D-tryptophyl-N-ε-tert-butoxy-carbonyl-lysyl-valine, methyl ester To a mixture of N-ε-tert-butoxycarbonyl-lysyl-valine, methyl ester (13 g, 36.1 mmol) in 200 mL THF was added fluorenylmethoxycarbonyl-D-tryptophan, N-hydroxysuccinimide ester (18.9 g, 36.1 mmol). Diisopropylethylamine was added to adjust the pH of the reaction mixture to pH 8, and the reaction stirred for 2 days. The solvent was then removed by evaporation and the residue redissolved in ethyl acetate, washed with 5% citric acid, saturated bicarbonate, and saturated brine, and then dried over sodium sulfate. The solution was then filtered and evaporated and the residue redissolved in ethyl acetate. The title compound was recovered from several crystallizations of this solution to give 17.3 g of product (22.5 mmol, 62% yield).

F. Synthesis of N-fluorenylmethoxycarbonyl-O-tert-butyltyrosine, N-hydroxy-succinimide ester To a solution of N-α-fluorenylmethoxycarbonyl-O-tert-butyltyrosine (25 g, 54.3 mmol) and N-hydroxysuccinimide (6.62 g, 57.5 mmol) in 250 mL dry THF cooled in a cold water bath was added diisopropylcarbodiimide (9.0 mL, 57.5 mmol). The reaction mixture was stirred overnight, filtered and the filtrate evaporated. The residue was then redissolved in toluene and hexanes. The title compound was isolated by filtration and dried to yield 27.7 g (49.7mmol, 92% yield).

G. Synthesis of N-fluorenylmethoxycarbonyl-O-tert-butyltyrosyl-D-tryptophyl-N-ε-tert-butoxycarbonyl-lysyl-valine, methyl ester Fluorenylmethoxycarbonyl-D-tryptophyl-N-ε-tert-butoxycarbonyl-lysyl-valine, methyl ester (17 g, 22.1 mmol) was treated with 40 mL diethylamine and 40 mL THF at room temperature for 1.5 h. The reaction mixture was then evaporated, resuspended in 100 mL THF and re-evaporated three times. The residue was taken up in 120 mL dry THF and N-fluorenylmethoxycarbonyl-O-tert-butyltyrosine, N-hydroxysuccinimide ester (12.3 g, 22.1 mmol) was added, followed by 20 mL dry THF and 4 mL diisopropylethylamine resulting in a solution having a pH of 9. After stirring overnight, the reaction was evaporated and the residue taken up in ethyl acetate. The ethyl acetate solution was washed with 5% citric acid, saturated sodium bicarbonate and saturated brine, then dried over magnesium sulfate and evaporated. The residue was taken up in ethyl acetate, ether and hexanes and the title compound precipitated. The precipitated compound was isolated by filtration and dried to yield 14.6 g of the title compound (14.8 mmol, 67% yield).

H. Synthesis of N-fluorenylmethoxycarbonyl-N-methylphenylalanine, N-hydroxysuccinimide ester To a solution of N-α-fluorenylmethoxycarbonyl-N-methylphenylalanine (25 g, 62.3 mmol) and N-hydroxysuccinimide (7.5 g, 65 mmol) in 180 mL dry THF cooled in a cold water bath was added diisopropylcarbodiimide (10 mL, 64.2 mmol). The reaction mixture was stirred overnight, filtered and the filtrate evaporated. The residue was then redissolved in toluene and hexanes. The title compound was isolated by filtration and dried to yield 28.3 g (57 mmol, 91% yield).

I. Synthesis of N-fluorenyhnethoxycarbonyl-N-methylphenylalanine-O-tert-butyl-tyrosyl-D-tryptophyl-N-ε-tert-butoxycarbonyl-lysyl-valine, methyl ester Fluorenylmethoxycarbonyl-O-ter-butyl-tyrosyl-D-tryptophyl-N-ε-tert-butoxycarbonyl-lysyl-valine, methyl ester (14 g, 14.2 mmol) was treated with 35 mL diethylamine and 35 mL THF at room temperature for 1 h. The reaction mixture was then evaporated, resuspended in 100 mL THF and re-evaporated three times. The residue was taken up in ethyl acetate and hexanes. The product, O-tert-butyltyrosyl-D-tryptophyl-N-ε-tert-butoxycarbonyl-lysyl-valine, methyl ester was precipitated, isolated by filtration and dried to yield 9.7 g (12.7 mmol, 90% yield). The O-tert-butyltyrosyl-D-tryptophyl-N-ε-tert-butoxycarbonyl-lysyl-valine, methyl ester was dissolved in 35 mL dry THF and N-fluorenylmethoxycarbonyl-N-methylphenylalanine, N-hydroxysuccinimide ester (6.35 g, 14.2 mmol) was added, followed by 3 mL diisopropyl-ethylamine resulting in a solution having a pH of 9. After stirring overnight, the reaction was evaporated and the residue taken up in ethyl acetate. The ethyl acetate solution was washed with 5% citric acid, saturated sodium bicarbonate and saturated brine, then dried over magnesium sulfate and evaporated. The residue was taken up in ethyl acetate, ether and hexanes and the title compound precipitated. The precipitated compound was isolated by filtration and dried to yield 12.4 g of the title compound (11.5 mmol, 81% yield).

J. Synthesis of N-fluorenylmethoxycarbonyl-S-tritylthomocysteine a. To about 400 mL liquid ammonia cooled to −78° C. in a dry ice/ethanol bath was added small amounts of elemental sodium followed by a sufficient amount of homocysteine to quench the resulting blue color of the sodium/ammonia solution until 5.7 g (248 mmol) sodium and 9.75 g (36.3 mmol) homocysteine had been consumed and the blue color of the sodium/ammonia solution persisted for about 15 min. Ammonium chloride (0.5 g) was added to quench the final blue color, and then the reaction was removed from the cooling bath and the ammonia allowed to evaporate under an argon stream. The flask was warmed slightly to drive off essentially all residual ammonia.

To the residue was added triphenylmethanol (23.6 g, 91 mmol) and the reaction flask cooled in an ice/water bath. 250 mL trifluoroacetic acid (TFA) was added, and after 30 min the mixture was evaporated and the residue redissolved and re-evaporated three times with chloroform. The residue was then redissolved in 300 mL water and the pH adjusted to pH 4 with 5% citric acid and 1M KOH. The product precipitated as a gum and was collected by filtration. The residue was then triturated with ether to yield S-trityl-homocysteine (7 g, 18.6 mmol, 26% yield). A second crop was isolated from the filtrate by crystallization from dimethylformamide (DMF)/ water to give a combined yield of 24.2 g (64 mmol, 89%).

b. To a solution of S-trityl-homocysteine (20 g, 53 mmol) in 150 mL acetone/100 mL water was added sodium carbonate (11.5 g, 109 mmol) and then O-fluorenylmethyl-O'-(N-succinimidyl) carbonate (17.5 g, 52 mmol) dissolved in 200 mL acetone, these additions being made over the course of about 1 h. The reaction mixture was then stirred for about 2 days and then the organic solvents were evaporated. To the aqueous residue was added 300 mL ethyl acetate and the mixture was acidified with 1M HCl. The organic phase was separated and washed sequentially with 1M HCl, 0.5M HCl, and 0.25M HCl, then dried over magnesium sulfate, filtered and evaporated. The crude product was chromatographed on silica gel (100% chloroform→3% methanol in chloroform) to yield the title compound (19.4 g, 32 mmol, 62% yield).

K. Synthesis of N-fluorenylmethoxycarbonyl-S-trityl-homocysteine-N-methyl-phenylalanine-O-tert-butyltyrosyl-D-tryptophyl-N-ε-tert-buto xycarbonyl-lysyl-valine, methyl ester Fluorenylmethoxycarbonyl-N-methylphenylalanine-O-tert-butyl-tyrosyl-D-tryptophyl-N-ε-tert-butoxycarbonyl-lysyl-valine, methyl ester (9.8 g, 8.5mol) was treated with 28 mL diethylamine and 30 mL THF at room temperature for 1 h. The reaction mixture was then evaporated, resuspended in 100 mL THF and re-evaporated three times. The residue was taken up in ethyl acetate and hexanes. The product, N-methylphenylalanine-O-tert-butyltyrosyl-D-tryptophyl-N-ε-tert-butoxycarbonyl-lysyl-valine, methyl ester was precipitated, isolated by filtration and dried to yield 4.9 g (8.1 mmol, 95% yield).

To a solution of N-fluorenylmethoxycarbonyl-S-trityl-homocysteine in 50 mL dry THF cooled in a −15° C. cooling bath was added N, N'-bis(2-oxo-3-oxazolidinyl)phosphinic chloride (BOP-Cl; 2.47 g, 9.7 mmol) and 1.7 mL diisopropylethylamine (9.7 mmol) and the reaction mixture was stirred for 30 min. N-methylphenylalanine-O-tert-butyltyrosyl-D-tryptophyl-N-ε-tert-butoxycarbonyl-lysyl-valine, methyl ester (7.48 g) in 50 mL dry THF was added, followed by an additional 1.7 mL diisopropylethylamine. The reaction volume was reduced 50% by evaporation and then stirred for 2 days at room temperature. The solvent was removed by evaporation and the residue redissolved in ethyl acetate, washed with 5% citric acid, saturated sodium bicarbonate and saturated brine, and dried over magnesium sulfate. The residue was taken up in ethyl acetate, ether and hexanes and the title compound precipitated. The precipitated compound was isolated by filtration to give 10.2 g (6.77 mmol, 84% yield).

L. Synthesis of S-trityl-homocysteine-N-methylphenylalanine-O-tert-butyl-tyrosyl-D-tryptophyl-N-ε-tert-butoxycarbonyl-lysyl-valine A solution of N-fluorenylmethoxycarbonyl-S-trityl-homocysteine-N-methylphenylalanine-O-tert-butyl-tyrosyl-D-tryptophyl-N-ε-tert-butoxycar bonyl-lysyl-valine, methyl ester (10 g, 6.6 mmol) and LiOH.2H$_2$O in 50 mL THF and 4 mL water was stirred for 3 days. An additional 25 mol% LiOH.2H$_2$O was added, and two hours later the solvent was evaporated and the residue redissolved in ethyl acetate. This solution was then washed with 5% citric acid, saturated sodium bicarbonate, and saturated brine, dried over magnesium sulfate, filtered and evaporated. The residue was redissolved in ethyl acetate, ether and hexanes and the title compound precipitated and was isolated by filtration and dried. The resulting impure product was flash chromatographed in silica gel using chloroform/10% methanol in chloroform to yield 3.46 g of the pure title compound (47 mmol, 41% yield).

M. Synthesis of cyclo-N-methylphenylalanine-O-tert-butyltyrosvl-D-tryptophyl-N-ε-tert-butoxycarbonyl-lysyl-valyl-S-tritvl-homocysteine A solution of S-trityl-homocysteine-N-methylphenylalanine-O-tert-butyl-tyroSyl-D-tryptophyl-N-ε-tert-butoxycarbonyl-lysyl-valine (3.42 g, 2.69 mmol) dissolved in 1740 mL DMF was cooled in an ice water bath, and 1.16 mL diisopropylethylamine and diphenyl phosphorylazide (DPPA; 5.4 g, 1. 16 mmol) were added. The reaction was incubated at −20° C. for 5 days and an additional 25 mol% DPPA was added, followed by an additional 100 mol% diisopropylethylamine. The DMF solvent was then removed by evaporation and the crude title compound crystallized from ethyl acetate, ether and hexanes to yield 2.43 g (1.9 mmol, 69%).

N. Synthesis of cyclo-N-methylphenylalanyl-tyrosyl-D-tryptophyl-lysyl-valyl-S-trityl-homocysteine cyclo-S-trityl-homocysteine-N-methylphenylalanine-O-tert-butyl-tyrosyl-D-tryptophyl-N-ε-tert-butoxycarbonyl-lysyl-valine (2.34 g, 1.9 mmol) was treated with 18.7 mL TFA, 2 mL dichloromethane, 0.94 mL water, 0.47 mL ethanedithiol and 0.37 mL triisopropylsilane for 1 h at room temperature. TFA was removed by evaporation and the residue redissolved and re-evaporated from chloroform three times. The residue was then redissolved in 10 mL chloroform and poured into 400 mL cold ether. The crude product precipitate was collected by filtration and purified by C18 preparative reverse phase HLPC (using a gradient of 30% acetonitrile→ 60% acetonitrile in water, all solvents containing 0.1% TFA) to give the title compound (1 g, 1.2 mmol, 62% yield). Fast atom bombardment mass spectrometry (FABMS) analysis gave a MH$^+$of 855, compared with the theoretical (average) predicted value of 855.09.

O. Synthesis of cyclo-N-methylphenylalanyl-tyrosyl-D-tryptophyl-lysyl-valyl-S-trityl-homocysteine, S-2-acetyl-glycyl-glycyl-cysteinyl-lysinamide (P587)

cyclo-N-methylphenylalanyl-tyrosyl-D-tryptophyl-lysyl-valyl-homocysteine (250mg, 0.29 mmol) and 2-chloroacetyl-glycyl-glycyl-S-trityl-cysteinyl-lysylamide (prepared by SPPS as described in Example 1; 238 mg, 0.35 mmol) were dissolved in 7 mL acetonitrile and 7 mL of a solution of lOOmM sodium carbonate/ 0.5mM EDTA, pH10 and stirred overnight. The reaction mixture was then evaporated to dryness and deprotected in TFA containing triisopropylsilane as described above in Example 1. The title compound was then purified by reverse phase HLPC to yield 92.4% of the expected theoretical yield. Fast atom bombardment mass spectrometry analysis gave a MH$^+$of 1258, compared with the theoretical (average) predicted value of 1257.70.The structure of this product, termed P587, is represented by the formula:

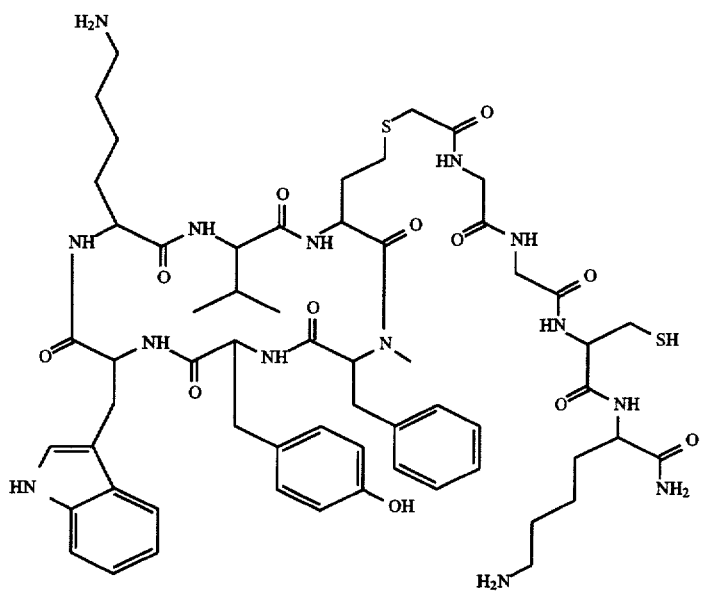

EXAMPLE 3

General Methods for Radiolabeling 0.1 mg of a peptide reagent prepared as in Example 1 was dissolved in 0.1 mL of water, or 0.9% sodium chloride, or 10% hydroxypropylcyclodextrin (HPCD), or 50:50 ethanol:water, or phosphate-buffered saline (PBS), or 50 mM potassium phosphate buffer (pH=5, 6 or 7.4). Tc-99m gluceptate was prepared by reconstituting a Glucoscan vial (E. I. DuPont de Nemours, Inc., Wilmington, Del.) with 1.0 mL of Tc-99m sodium pertechnetate containing up to 200 mCi and allowed to stand for 15 minutes at room temperature. 25 μL of Tc-99m gluceptate was then added to the reagent and the reaction allowed to proceed at room temperature or at 100° C. for 5–30 min and then filtered through a 0.2 μm filter.

The Tc-99m labeled peptide reagent purity was determined by HPLC using the following conditions: a Waters Delta-Pak RP-18 analytical column, having dimensions of 5μm ×4.6 mm×220 mm, was loaded with each radiolabeled peptide, which were then eluted at a solvent flow rate of 1 mL/min. Gradient elution was performed over 10–20 min using a linear gradient beginning with 100% Solvent A (0.1% TFA/water) and ending with 100% Solution B (0.1% TFA/90% acetonitrile/water). Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

The following Table illustrates successful Tc-99m labeling of peptides prepared according to Example 1 using the method described herein.

TABLE I

| Peptides | FABMS MH+ | Radiochemical Yield(%)* | HPLC R$_T$(min) |
|---|---|---|---|
| cyclo(N-methyl)FYW$_D$KV.Hcy.(CH$_2$CO.GGC.amide) | 1129 | 98[2] | 15.1, 17.2 |
| cyclo(N-methyl)FYW$_D$KV.Hcy.(CH$_2$CO.GGCK.amide) | 1258 | 99[2] | 15.0 |
| cyclo(N-methyl)FYW$_D$KV.Hcy.(CH$_2$CO.GGCR.amdide) | 1285 | 99[1] | 15.1 |
| cyclo(N-methyl)FYW$_D$KV.Hcy.(CH$_2$CO.GGCKK.amide) | 1386 | N.D. | N.D. |
| cyclo(N-methyl)FYW$_D$KV.Hcy.(CH$_2$CO.GGC.Orn.amide) | 1244 | 98[3] | 7.0 |

*Superscripts refer to the following labeling conditions:
[1] = in 10% HPCD at room temperature
[2] = in 50/50 ethanol/water at room temperature
[3] = in 0.9% NaCl at 100° C.
HPLC methods (indicated by superscript after R$_T$):
Waters-1 column, 100% Solution A → 100% Solution B in 10 min Single-letter abbreviations for amino acids can be found in Zubay, ibid. p.33. Underlining indicates the formation of an amide or a thiol linkage between the linked amino acids of derivative groups. Acm is acetamidomethyl; Orn is ornithine; F$_D$ is phenylalanine; Y$_D$ is D-tyrosine; W$_D$ is D-tryptophan; Apc = L-[S-(3-aminopropyl)cysteine; and Hcy is homocysteine.

Radioiodination and radioaststination are performed as described by Seevers et al. (1982, Chem. Rev. 82: 575–590).

Non-radioactive rhenium complexes were prepared by co-dissolving each of the peptide reagents of the invention with about one molar equivalent of tetrabutylammonium oxotetra- bromorhenate (+5), prepared as described by Cotton et al. (1966, Inorg. Chem. 5: 9–16) in dimethylformamide or acetonitrile/water and stirred for 0.5–5 days. The rhenium complexes were isolated by reverse phase HPLC as described above for Tc-99m labeled peptides and were characterized by FABMS or ESMS.

Radioactive rhenium complexes, using for example Re-186 or Re-188, are prepared from the appropriate perrhenate salts using the same protocol as for Tc-99m labeling, or by adding a reducing agent to a solution of the peptide and perrhenate, or optionally using a ligand transfer agent such as citrate and incubating the reaction at a temperature between room temperature and 100° C. for between 5 and 60 min.

EXAMPLE 4

Inhibition of [$^{125}$I-Tyr$^{11}$]Somatostatin-14 Binding to AR42J Rat Pancreatic Tumor Cell Membranes The ability of various somatostatin receptor-binding reagents of the invention to bind to somatostatin receptors in vitro was demonstrated in an assay of peptide reagent-mediated inhibition of binding of a radiolabeled somatostatin analogue to somatostatin receptor-containing cell membranes.

The rat pancreatic tumor cell line AR42J expressing the somatostatin receptor was cultured in Dulbecco's modified essential media (DMEM) supplemented with 10% fetal calf serum (FCS) and 8mM glutamine in a humidified 5% $CO_2$ atmosphere at 37° C. Harvested cells were homogenized in cold buffer (50 mM Tris-HCl, pH 7.4), and the homogenate was then centrifuged at 39,000 g for 10 min at 4° C. Pellets were washed once with buffer and then resuspened in ice-cold 10 mM Tris-HCl buffer (pH 7.4). Equal aliquots of this cell membrane preparation were then incubated with [$^{125}$I-Tyr$^{11}$]somatostatin-14 (Amersham, Arlington Heights, Ill.) at a final concentration of 0.5 nM at 750,000 cpm/mL, specific activity 2000 Ci/mmol and either a peptide or peptide-rhenium complex of the invention (at a final concentration ranging from $10^{-11}$M to $10^{-6}$M in 50 mM HEPES buffer, pH 7.4, containing 1% bovine serum albumin, 5 mM $MgCl_2$, 0.02 mg/mL bacitracin, 0.02 mg/mL phenylmethylsulfonylfluoride and 200,000 IU Trasylol for 25 min at 30° C.

After incubation, this membrane mixture was filtered through a polyethyleneimine-washed GC/F filter (Whatman Ltd., Maidstone, England) using a filtration manifold, and the residue remaining on the filter was washed three times with 5 mL cold HEPES buffer. The filter and a sample of the filter washings were then counted on a gamma counter. To assess non-specific binding, the assay was also performed essentially as described in the presence of 200 nm unlabeled somatostatin-14. Data analysis included Hill plots of the data to yield inhibition constants as described by Bylund and Yamamura (1990, *Methods in Neuro-transmitter Receptor Analysis*, Yamamura et al., eds., Raven Press: N.Y.). The results obtained using this assay with the reagents of the invention are as follows:

TABLE II

| Peptide | $K_i$(nM) |
|---|---|
| cyclo(N-methyl)FYW$_D$KV.Hcy.(CH$_2$CO.GGCKK.amide) | 0.26 |
| cyclo(N-methyl)FYW$_D$KV.Hcy.(CH$_2$CO.GGCK.amide) | 2.5 |
| cyclo(N-methyl)FYW$_D$KV.Hcy.(CH$_2$CO.GGC.amide) | 2.6 |

These results demonstrate that peptide reagents of the invention bind with high affinity to somatostatin receptors in vitro.

EXAMPLE 5

Localization and In Vivo Imaging of Somatostatin Receptor (SSTR)-Expressing Tumors in Rats In vivo imaging of somatostatin receptors expressed by rat tumor cells was performed essentially as described by Bakker et al. (1991, *Life Sciences* 49: 1593–1601).

CA20948 rat pancreatic tumor cells, thawed from frozen harvested tumor brei, were implanted intramuscularly in a suspension of 0.05 to 0.1 mL/animal, into the right hind thigh of 6 week old Lewis rats. The tumors were allowed to grow to approximately 0.5 to 2 g, harvested, and tumor brei was used to implant a second, naive set of Lewis rats. Passaging in this fashion was repeated to generate successive generations of tumor-bearing animals. The tumor-bearing animals used for the in vivo studies were usually from the third to fifth passage and carried 0.2 to 2 g tumors.

For studies of the specificity of radiotracer localization in the tumors, selected animals were given an subcutaneous SSTR-blocking dose (4 mg/kg) of octreotide 30 minutes prior to injection of the radiotracer. (This protocol has been shown by Bakker et al. to result in a lowering of $^{111}$In-[DTPA]octreotide tumor uptake by 40%.)

Third- to fifth-passage CA20948 tumor-bearing Lewis rats were restrained and injected intravenously via the dorsal tail vein with a dose of 0.15–0.20 mCi $^{99m}$Tc-labeled peptide corresponding to 3 to 8 µg peptide in 0.2 to 0.4 mL.

At selected times, the animals were sacrificed by cervical dislocation and selected necropsy was performed. Harvested tissue samples were weighed and counted along with an aliquot of the injected dose in a gamma well-counter.

The 90-minute biodistribution results of selected radiolabeled peptides are presented in Table I. Notably, $^{99m}$Tc-P587, $^{99m}$Tc-P617, $^{99m}$Tc-P726, and $^{99m}$Tc-P736 showed very high tumor uptake and tumor/blood ratios demonstrating their high specific uptake in target (tumor) tissue.

FIG. 1 shows an image of $^{99m}$Tc-P587 in a tumor-bearing rat. The high uptake in the tumor in the lower leg (arrow) is clearly visible.

$^{99m}$Tc-P587 uptake in tumors in rats was compared with and without pre-injection treatment with octreotide, a somatostatin analogue known to bind to the somatostatin receptor in vivo. In these experiments, receptor-blocking by administration of octreotide prior to administration of $^{99m}$Tc-P587 reduced specific tumor uptake of the radiolabeled peptide by 76%. These results confirmed that binding of $^{99m}$Tc-P587 in vivo was SSTR-specific.

TABLE III

| No. | Peptides | % ID/g Tumor | Blood | Tumor/Blood |
|---|---|---|---|---|
| P736 | cyclo(N-methyl)FYW$_D$KV.Hcy.(CH$_2$CO.GGCRK.amide) | 2.1 | 0.24 | 9 |
| P587 | cyclo(N-methyl)FYW$_D$KV.Hcy.(CH$_2$CO.GGCK.amide) | 3.4 | 0.61 | 6 |
| P617 | cyclo(N-methyl)FYW$_D$KV.Hcy.(CH$_2$CO.GGCR.amide) | 6.7 | 0.73 | 9 |
| P726 | cyclo(N-methyl)FYW$_D$KV.Hcy.(CH$_2$CO.KKC.amide) | 2.5 | 0.30 | 8 |

EXAMPLE 6
In Vivo Imaging of Human Somatostatin Receptor (SSTR)-Expressing Tumors with Tc-99m Labeled P587

In a clinical trial, scintigraphic imaging of human patients bearing SSTR-expressing tumors was achieved using the Tc-99m labeled P587 reagent.

A total of 10 patients, four females and six males ranging in age from 27 to 69 years, had been previously diagnosed with growth hormone-secreting pituitary adenoma (4 patients), melanoma (1 subject), medullary thyroid cancer (1 subject), small cell lung carcinoma (SCLC; 1 patient), non-Hodgkin's lymphoma (1 patient) or gastric carcinoid (1 patient). Each of these patients were administered Tc-99m labeled P587 at a dose of 10–22 mCi per 0.2–0.5 mg by intravenous injection. Scintigraphic imaging was them performed as described herein on each patient for 4 hours post-injection.

Gamma camera imaging is started simultaneously with injection. Anterior images were acquired as a dynamic study (10 sec image acquisitions) over the first 10 min, and then as static images at 1, 2, 3 and 4 h post-injection. Anterior images were acquired for 500,000 counts or 20 min (whichever is shorter), at approximately 10–20 min, and at approximately 1, 2, 3 and 4 h post-injection.

The scintigraphic imaging agent was found to clear rapidly from the bloodstream, resulting in less than 10% of the injected dose remaining in the circulation within 30 minutes of injection. This allowed image acquisition of tumor sites to be achieved as early as 15–30 min after injection of scintigraphic imaging agent. All known tumors were detected in this study, as well as two previously-undetected metastatic lesions which were later confirmed using computer-assisted tomography (CAT scan).

These results demonstrated that the scintigraphic imaging agents of this invention were highly effective in detecting SSTR-expressing primary and metastatic tumors in humans in vivo.

It should be understood that the foregoing disclosure emphasizes certain specific embodiments of the invention and that all modifications or alternatives equivalent thereto are within the spirit and scope of the invention as set forth in the appended claims.

What is claimed is:

1. A composition of matter comprising a specific binding peptide covalently linked to a metal ion-complexing moiety, wherein the peptide specifically binds to somatostatin receptors, and having formula:

cyclo(N-CH$_3$)-Phe-Tyr-(D-Trp)-Lys-Val-Hcy.(CH$_2$CO.X)

wherein X is a metal ion complexing moiety having formula (amino acid)$_n$-B-(amino acid)$_m$-Z, wherein B is a thiol-containing moiety that is cysteine, homocysteine, isocysteine, or penicillamine;

(amino acid)$_n$ and (amino acid)$_m$ are each independently any primary α- or β-amino acid that does not comprise a thiol group;

Z is —OH or —NH$_2$;

n is an integer between 2 and 5; and m is an integer between 0 and 5.

2. A composition of matter according to claim 1 having the formula:

cyclo(N-methyl)FYW$_D$KV.Hcy.(CH$_2$CO.GGCK.amide).

3. A composition of matter according to claim 1 selected from the group consisting of:

cyclo(N-methyl)FYW$_D$KV.Hcy.(CH$_2$CO.GGCR.amide)

cyclo(N-methyl)FYW$_D$KV.Hcy.(CH$_2$CO.GGCRD.amide)

cyclo(N-methyl)FYW$_D$KV.Hcy.(CH$_2$CO.GGCRK.amide)

cyclo(N-methyl)FYW$_D$KV.Hcy.(CH$_2$CO.GGCRR.amide)

cyclo(N-methyl)FYW$_D$KV.Hcy.(CH$_2$Co.GGCKK.amide) and cyclo(N-methyl)FYW$_D$KV.Hcy.(CH$_2$CO.KKC.amide).

4. A reagent for preparing a scintigraphic imaging agent for imaging a site within a mammalian body, comprising the composition of matter of claim 1.

5. A scintigraphic imaging agent comprising the reagent according to claim 4 wherein the radiolabel binding moiety is bound to technetium-99m.

6. A kit for preparing a radiopharmaceutical preparation, said kit comprising a sealed vial containing a predetermined quantity of the reagent of claim 4 and a sufficient amount of reducing agent to label the reagent with technetium -99m.

7. The composition of matter of claim 1 wherein the metal ion-complexing moiety is bound to a metal ion.

8. The composition of matter of claim 7 wherein the metal is rhenium, zinc or tin.

9. The composition of matter of claim 1 wherein the metal ion-complexing moiety is bound to a beta-particle emitting metal ion.

10. The composition of matter of claim 9 wherein the beta-particle emitting metal is rhenium-186 or rhenium-188.

11. The composition of matter of claim 1 wherein the metal ion-complexing moiety is bound to a conversion electron emitting metal ion.

12. The composition of matter of claim 11 wherein the conversion electron emitting metal is tin-117m.

13. A composition of matter according to claim 1 that is radioactively labeled with iodine- 125, iodine-131 or astatine-211.

14. A reagent for preparing a diagnostic agent for localizing a site within a mammalian body, comprising the composition of matter of claim 1.

15. A diagnostic agent comprising the reagent according to claim 14 wherein the metal ion complexing moiety is bound to a paramagnetic metal ion.

16. The diagnostic agent of claim 15 wherein the paramagnetic metal is iron or copper.

17. A diagnostic agent comprising the reagent according to claim 14 bound to a superparamagnetic particle.

18. A diagnostic imaging agent comprising the composition of claim 1 radiolabeled with iodine 123, iodine-125 or iodine-131.

19. A composition of matter having formula:

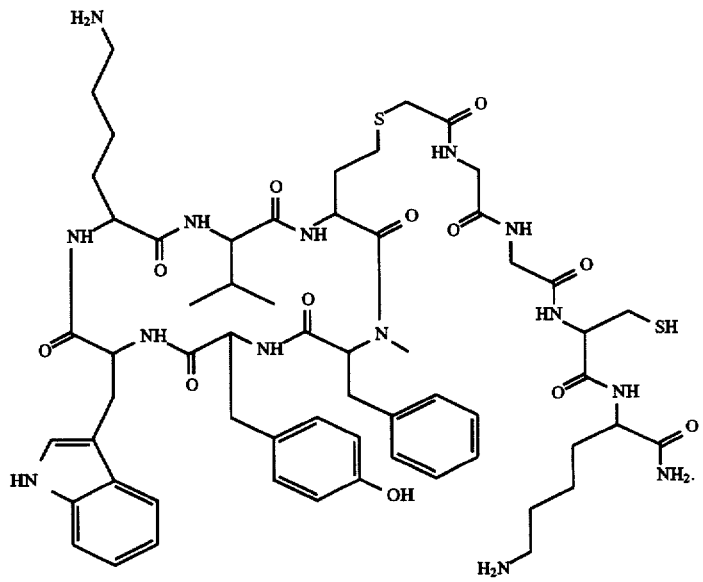

20. A composition of matter according to claim 19 that is radiolabeled with technetium-99m.

21. The reagent of claim 4 wherein the imaged site within a mammalian body is a site of a primary or metastatic, somatostatin receptor-expressing tumor.

22. An article of manufacture comprising a sealed vial containing a predetermined quantity of the composition of matter of claim 19 and a sufficient amount of reducing agent to label the composition with technetium-99m.

23. A kit for preparing a radiopharmaceutical preparation, said kit comprising a sealed vial containing a predetermined quantity of the reagent of claim 19 and a sufficient amount of reducing agent to label the reagent with technetium-99m.

* * * * *